US00PP37840P3

(12) United States Plant Patent
Valin

(10) Patent No.: US PP37,840 P3
(45) Date of Patent: Nov. 3, 2026

(54) ***COSMOS* PLANT NAMED 'VG001'**

(50) Latin Name: *Cosmos atrosanguineus*
Varietal Denomination: VG001

(71) Applicant: Valin Genetics Limited, Exeter (GB)

(72) Inventor: Charles Valin, Exeter (GB)

(73) Assignee: Valin Genetics Limited, Exeter (GB)

( * ) Notice: Subject to any disclaimer, the term of this patent is extended or adjusted under 35 U.S.C. 154(b) by 0 days.

(21) Appl. No.: 19/060,779

(22) Filed: Feb. 23, 2025

(65) Prior Publication Data

US 2026/0256036 P1 Aug. 27, 2026

(51) Int. Cl.
*A01H 5/02* (2018.01)
*A01H 6/14* (2018.01)

(52) U.S. Cl.
USPC ..... Plt./418
CPC ..... *A01H 6/14* (2018.05); *A01H 5/02* (2013.01)

(58) Field of Classification Search
USPC ..... Plt./263.1, 418
See application file for complete search history.

(56) References Cited

U.S. PATENT DOCUMENTS

PP21,879 P3 * 4/2011 Poulter ..... A01H 6/14
Plt./418

* cited by examiner

*Primary Examiner* — Karen M Redden
(74) *Attorney, Agent, or Firm* — Weatherly IP Solutions, LLC; James M. Weatherly

(57) ABSTRACT

A new cultivar of *Cosmos* plant named 'VG001' that is distinguishable by its compact mounded foliage comprised of compound leaves each with 7 leaflets in 3 opposite pairs and one terminal leaflet and bearing multiple slender flower stems bearing cherry-red colored single inflorescences. The inflorescence of 'VG001' is a capitulum consisting of an outer whorl of 8 elliptic sterile cherry-red colored ray flowers and an inner whorl of 55 to 65 disc florets massed in a receptacle. The inflorescences of 'VG001' are pleasantly fragrant and reminiscent of chocolate or dark cocoa powder. The apices of the five stigmas of the disc florets of 'VG001' are recurved and are presented in a star-shaped pattern and protruding for approximately 2 mm above the corolla tube apex. Plants of 'VG001' are hardy in USDA Zones 9 and higher.

2 Drawing Sheets

Figure 1:
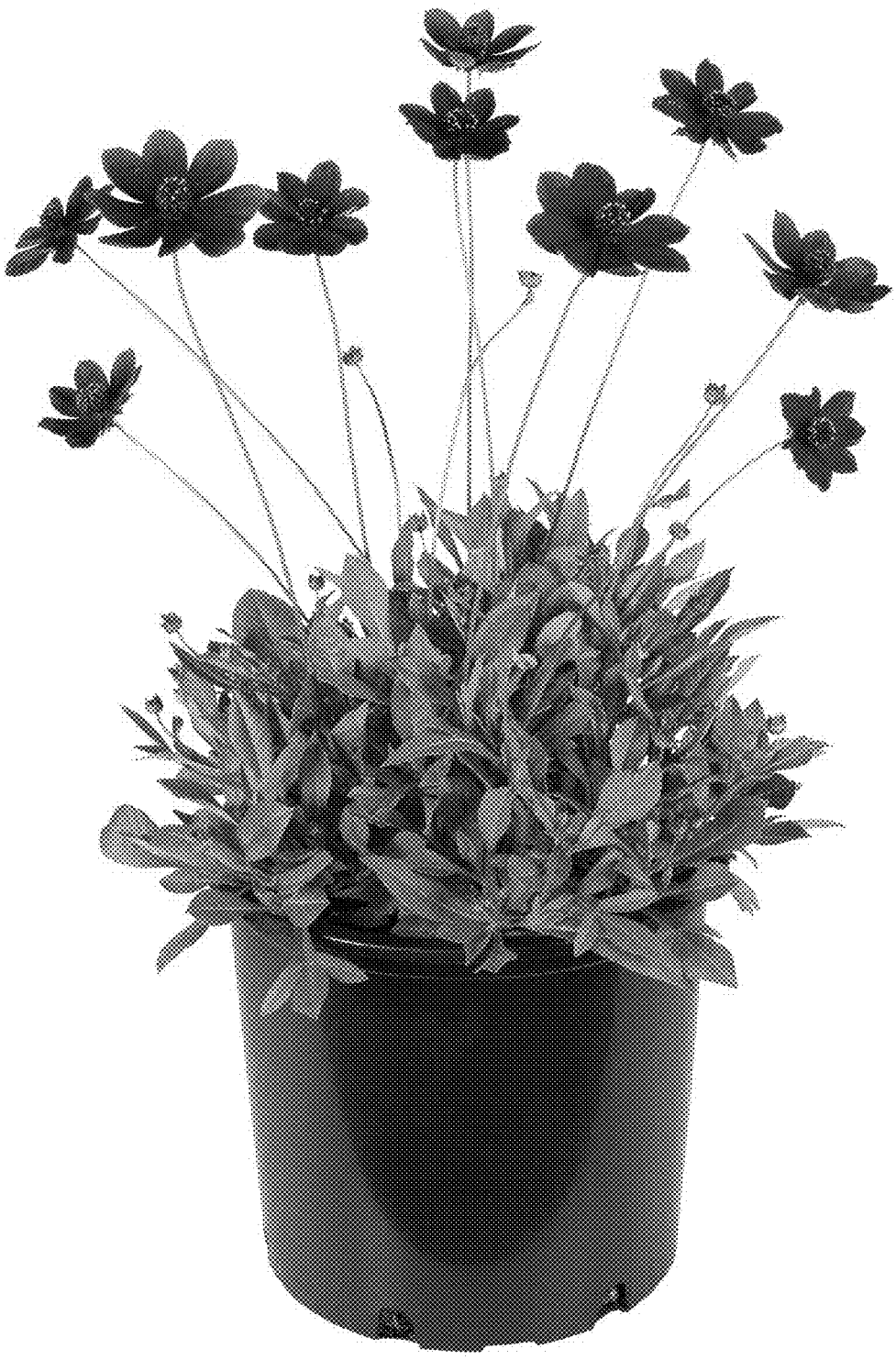

Genus and species: *Cosmos atrosanguineus.*
Variety denomination: 'VG001'.

BACKGROUND OF THE INVENTION

The present invention relates to a new and distinct cultivar of *Cosmos* grown for use in containers, in mixed combinations, garden beds and in the landscape. The new invention is known botanically as *Cosmos atrosanguineus* and will be referred to hereinafter by the cultivar name 'VG001'. *Cosmos atrosanguineus* is commonly known as chocolate *Cosmos* in recognition of the pronounced chocolate fragrance of its flowers.

The genus *Cosmos* is in the family Compositae. The inflorescence of 'VG001' is a capitulum consisting of a single outer whorl of eight ray florets, and an inner whorl of 55 to 65 petaloid stamens forming disc florets massed in a receptacle.

In 2019, the inventor commenced a breeding program at the inventor's nursery in Woodbridge, Suffolk, United Kingdom with the aim of developing novel flower colors. The inventor assembled a collection of *Cosmos* species and cultivars for performing controlled pollinations. In 2020, the inventor performed a controlled pollination of an unnamed *Cosmos atrosanguineus* (not patented) as female parent by an unnamed male fertile plant of *Cosmos atrosanguineus* selected from the inventor's collection of species and cultivars. A small number of seeds resulted and were collected from the female parent. The collected seeds were sown and grown-on to flowering stage, and evaluated for novel color of flower and for floriferousness of the new seedlings. The inventor selected one seedling, known to the inventor as CS20000-1, The collected seeds were sown and grown on to produce sufficiently aged plants for the inventor to select one seedling for its combination of larger flowers, unique flower color and its floriferousness and named this seedling 'VG001'.

The first asexual reproduction of 'VG001' was conducted by the inventor in fall 2021 using vegetative cuttings. The inventor transferred harvested cuttings of 'VG001' to a tissue culture laboratory for establishing virus-free stock material and subsequent commercial tissue culture propagation.

The inventor received and grew the first tissue cultured plantlets for growing on to maturity. The inventor confirmed that the mature plants of 'VG001' exhibited the characteristics which had attracted the inventor to make the initial selection. The inventor has confirmed from growing asexually propagated plants of 'VG001' to maturity that 'VG001' is stable and uniform variety and reproduces true to type in subsequent generations of asexual propagation.

SUMMARY OF THE INVENTION

The following traits have been repeatedly observed and represent the distinguishing characteristics of the new *Cos-*

*mos* cultivar named 'VG001'. These traits in combination distinguish 'VG001' from all other existing varieties of *Cosmos* known to the inventor. 'VG001' has not been tested under all possible conditions and phenotypic differences may be observed with variations in environmental, climatic, and cultural conditions, however, without any variance in genotype.

1. 'VG001' exhibits compact mounded foliage with multiple slender flower stems bearing cherry-red colored single flowers.
2. One-year old and mature plants of 'VG001' are 30 cm in height excluding the flowers, and 60 cm in height including the flowering stems and flowers. Plants of 'VG001' are 45 cm in width.
3. 'VG001' bears compound leaves each with 7 leaflets in 3 opposite pairs and one terminal leaflet.
4. The leaves and leaflets of 'VG001' are mid green in color.
5. The inflorescence of 'VG001' is a capitulum consisting of an outer whorl of 8 elliptic sterile cherry-red colored ray flowers and an inner whorl of 55 to 65 disc florets massed in a receptacle.
6. The florescences of 'VG001' are pleasantly fragrant and reminiscent of chocolate or dark cocoa powder.
7. The disc florets of 'VG001' are formed of 5 narrowly elliptic greyed-purple colored petals which are basally and longitudinally fused into a greyed-purple colored tube.
8. The apices of the five stigmas of the disc florets of 'VG001' are recurved and are presented in a star-shaped pattern and protruding for approximately 2 mm above the corolla tube apex.
9. Plants of 'VG001' are hardy in USDA Zones 9 and higher.

BRIEF DESCRIPTION OF THE PHOTOGRAPHS

Figure 2:
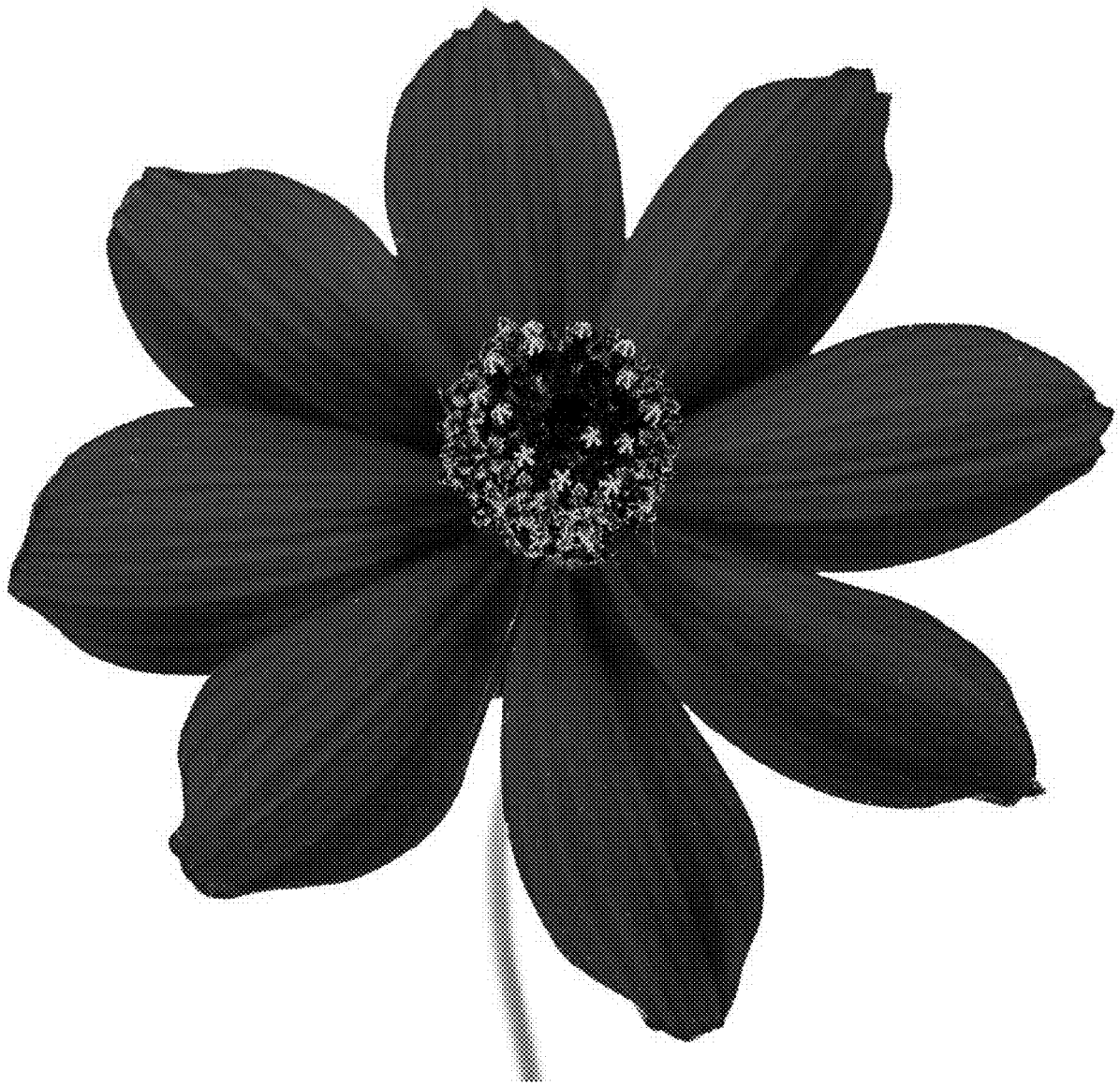

The accompanying color drawings labeled FIG. 1 and FIG. 2 illustrate the overall appearance of the new *Cosmos* cultivar named 'VG001' showing the colors as true as is reasonably possible to obtain in colored reproductions of this type. Colors in the photographs may differ from the color values cited in the detailed botanical description, which accurately describes the actual colors of the 'VG001'. The photographs were made from digital photographs of twelve four months old from a cutting-raised plant grown outdoors in Santa Barbara, California.

The drawing labeled FIG. 1 depicts the entire plant in bloom.

The drawing labeled FIG. 2 depicts a close-up view of the face of a flower of 'VG001'.

BOTANICAL DESCRIPTION OF THE PLANT

The following is a detailed botanical description of the new *Cosmos* cultivar named 'VG001'. Observations and measurements were collected in late August 2024 in Woodbridge, Suffolk, United Kingdom from 12 months old plants grown out of doors in a 2-gallon container. Color determinations were made in accordance with the 2019 edition of The Royal Horticultural Society Colour Chart from London, England, except where general color terms of ordinary dictionary significance are used. Growing requirements are similar to the species.

Botanical classification: *Cosmos atrosanguineus* 'VG001'.

*Family*.—Compositae.

*Genus*.—*Cosmos*.

*Species*.—*Atrosanguineus*.

*Denomination*.—'VG001'.

*Common name*.—*Cosmos*.

*Parentage*.—Female parent: Unnamed and unreleased *Cosmos atrosanguineus* plant (not patented). Male parent: An unnamed and unreleased male fertile plant of *Cosmos atrosanguineus* selected from the inventor's collection of species and cultivars.

*Propagation method*.—Tissue culture and cuttings from virus-indexed mother stock.

*Rooting system*.—Fine and fibrous.

*Vigor*.—Vigorous, naturally self-branching.

*Habit*.—Upright habit.

*Use*.—For use in containers, in mixed combinations, beds and the landscape.

*Type*.—Annual in most regions, perennial in USDA Zone 9 and warmer.

*Dimensions at 12 months of age and in subsequent years*.—55 cm in height including flowering stems and flowers, and 35 cm in width across the foliage mound.

*Cultural requirements*.—Grow in full sun with regular water, and well-draining potting soil.

*Pest susceptibility*.—Susceptible to aphids (*Aphis gossypii*) when stressed.

*Disease susceptibility*.—Susceptible to powdery mildew (*Erysiphacea* spp.) in humid conditions.

*Hardiness*.—USDA Zone 9 and higher.

Propagation: Tissue culture micropropagation of vegetative cuttings taken from indexed virus-free mother stock held in vitro.

*Rooting, root system*.—Vegetative cuttings whether tissue cultured or traditional cuttings are readily rooted in mist systems and a rooting medium temperature ranging between 20° C. and 23° C.

*Roots*.—Fine, dense, fibrous becoming tuberous late in the season.

Branching, stems:

*Branching*.—Basal stems arise from the root system including from any tubers which have formed. Branches grow rapidly in early spring.

*Branch and stem quantity*.—3 to 5 basal branches arise from the root system and 6 or more secondary branches are borne on each basal branch.

*Branch stem shape*.—Cylindrical.

*Branch stem dimensions*.—15 cm in length and 2.75 mm in diameter.vm.

*Internode distance*.—Ranges between 5 cm and 7 cm.

*Branch stem color*.—187A.

*Surface*.—Sparsely hirsute.

*Branch stem color*.—187A.

Foliage:

*Leaf arrangement*.—Opposite.

*Leaf attachment*.—Petiolate.

*Petiole dimensions*.—6 mm in length, 3 mm in diameter.

*Petiole shape*.—Concave.

*Petiole surface*.—Smooth.

*Petiole color*.—NN137A except petiole margins and midrib dark greyed-purple 187D.

*Leaf type*.—Compound leaves consisting typically of 7 leaflets arranged as three lower opposite pairs and one terminal lanceolate leaflet.

*Leaflet apex, base*.—Acute.
*Leaflet base*.—Acuminate.
*Leaflet margin*.—Smooth, entire.
*Leaflet color* (*new foliage in spring, adaxial surface*).—137B.
*Leaflet color* (*new foliage in spring, abaxial surface*).—138B.
*Leaflet color* (*mature foliage, adaxial surface*).—NN137A.
*Leaflet color* (*mature foliage, abaxial surface*).—147B.
*Leaflet venation*.—Pinnate, veins color 146D becoming purple 187D (adaxial surface) and yellow-green 147D (abaxial surface) as leaf ages.
*Leaflet shape*.—Ovate (lower, opposite pairs), lanceolate (terminal leaflet).
*Leaf dimensions* (*overall*).—12 cm in length, 9 cm in width across lowest leaflets.
*Leaflet dimensions* (*in lowest pair*).—5.5 cm in length, 2.5 cm in width.
*Leaflet dimensions* (*in second pair*).—4 cm in length, 2 cm in width.
*Terminal leaflet dimensions*.—5.5 cm in length, 3.5 cm in width.
*Leaf and leaflet color* (*adaxial surfaces*).—N186A, greener in shade, towards 189A, and darker in sun or when first emerging, towards 202A.
*Leaf and leaflet color* (*abaxial surfaces*).—138B.
*Leaf and leaflet margins*.—Ciliate, hairs fine, tiny, less than 0.5 mm in length, color NN155D.
*Leaf and leaflet apex*.—Acute.
*Leaf and leaflet base*.—Truncate.
*Leaf and leaflet venation pattern*.—Pinnate.
*Vein color*.—Adaxial surface: As leaf except midrib 183D. Abaxial surfaces: Midrib 152A, lateral veins N137A.
*Leaf and leaflet surfaces* (*abaxial surfaces*).—Glabrous, matte.
*Leaf and leaflet surfaces* (*adaxial surfaces*).—Lightly pubescent, hairs 0.5 mm in length, color NN155D.
*Leaf attachment*.—Petiolate to first leaflet pair, petiole continues to base of second leaflet pair.

Petiole:
*Dimensions* (*stem to first leaflet pair*).—6 mm in length, 3 mm in width.
*Petiole shape*.—Sulcate.
*Petiole color*.—NN137A except margins and midrib 187D.
*Petiole surface*.—Faintly puberulent.

Inflorescence:
*Inflorescence type*.—Capitulum on each branch, consisting of a single outer whorl of sterile ray flowers, and an inner whorl of petaloid stamens, arranged around a central cluster or disc of disc florets.
*Aspect*.—Facing upward and outward.
*Inflorescence quantity*.—Ranges between 20 inflorescences in late spring and early summer flowering period and up to 50 inflorescences in mid-summer.
*Dimensions of inflorescence* (*average*).—2 cm in height and 6 cm to 9 cm in diameter.
*Inflorescence shape, aspect*.—Radiate with center disc, aspect vertical.
*Blooming seasons*.—In the United Kingdom, from end of May until October or first hard freeze. The peak flowering months are June to September.
*Fragrance*.—Pleasant, reminiscent of chocolate or dark cocoa powder.
*Lastingness of inflorescence*.—8 to 10 days until petal fall.
*Suitability for cutting*.—Inflorescences persist for 7 to 10 days on the plant and for 7 days off the plant after cutting.

Peduncle:
*Dimensions* (*average*).—25 cm in length and 3 mm in diameter.
*Angle*.—None, peduncles are extensions to lateral branches or flowering stems.
*Shape*.—Cylindrical.
*Strength*.—Stiff and wiry.
*Surface*.—Smooth with iridescent waxy bloom when observed from above.
*Peduncle color* (*waxy bloom*).—N186C.

Receptacle:
*Receptacle dimensions*.—2.5 cm in height, 0.5 cm in diameter.
*Receptacle surface*.—Glabrous.
*Receptacle color*.—147A.

Phyllaries:
*Description*.—Two concentric whorls of phyllaries, approximately 20 in number, subtend the receptacle. The inner whorl consists of eight membranous translucent phyllaries adpressed to the abaxial surface of each ray floret petal. A second outer whorl of phyllaries is attached at the base of the inner whorl. Phyllaries in the outer wall are free and strongly reflexed.
*Phyllary shape*.—Broadly lanceolate.
*Phyllary dimensions* (*larger phyllaries, mostly in outer whorl*).—20 mm in length and 8 mm in width.
*Phyllary dimensions* (*smaller phyllaries, mostly in inner whorl*).—11 mm in length and 3 mm to 6 mm in width. Texture: Membranous, translucent towards apex. Color (adaxial and abaxial surfaces): 160A at base becoming lighter towards apex, closest to 160D but lighter. Phyllary veins (both surfaces): Fine longitudinal parallel veins, vein color 53A. Phyllary shape: Apex: Rounded. Base: Truncate. Margin: Entire. Phyllary surface (both surfaces): Glabrous, waxy.

Bud:
*Shape*.—Globose.
*Dimensions* (*sepals about to open*).—15 mm in height and 20 mm in diameter.
*Surface*.—Glabrous, glossy.
*Color*.—Ranges between N186C and 187B.
*Apex*.—Obtuse.
*Base*.—Truncate.

Calyx: Absent.

Ray florets:
*Quantity per inflorescence*.—8.
*Arrangement*.—Radiate.
*Dimensions* (*average*).—35 mm in length and 19 mm in width.
*Ray floret shape*.—Obovate.
*Ray floret margin*.—Entire, except apex.
*Ray floret apex*.—Mostly rounded, apex occasionally tridentately lobed, in which case the central lobe (primary apex) protrudes by 2 mm to 3 mm.
*Ray floret base*.—Cuneate.

*Ray floret colors* (*adaxial surface*).—Ranges between 60A and 71A.

*Ray floret colors* (*abaxial surface*).—Ranges between 187B and 187C.

*Ray floret ribs or veins* (*adaxial surface*).—Raised longitudinal ribs colored as adaxial surface. No veins apparent.

*Ray floret ribs or veins* (*abaxial surface*).—Longitudinal depressions colored as abaxial surface. Longitudinal veins fine, parallel, darker than abaxial surface, color N187A.

*Ray floret surface* (*both surfaces*).—Smooth, glabrous.

Disc florets:

*Description*.—Disc florets massed in the center of the receptacle to form the central inflorescence disc. Younger inner disc florets (stigmas not exposed) consist of five dark purple fused disc floret petals. Fully developed disc florets exhibit prominently exserted yellow bifurcated recurved stigmas.

*Receptacle diameter*.—22 mm.

*Disc color*.—Initially, dark red 53A (only young disc floret ray florets visible) becoming deep yellow 17B as disc florets open (from circumference then inwards) and the yellow stigmas become prominent.

*Quantity of disk florets*.—55 to 65 disc florets per receptacle.

*Disc floret shape*.—Tubular, five longitudinally fused petals.

*Disc floret tube dimensions*.—9 mm in length, 3 mm in diameter and 5 mm in diameter measured across apices.

*Disc floret petals and tube color* (*both surfaces*).—Uppermost section: (above the center of the tube): Ranges between N186C and 187A. Lowermost section (below center of tube and nearer to base): 150D. Disc floret petal surface: Glabrous, glossy.

Reproductive organs (Androecium present on disc florets only):

*Stamens*.—5 in number, fused at base.

*Filament dimensions*.—6 mm in length, less than 0.5 mm in diameter.

*Filament color*.—150D.

*Anthers*.—Shape: Cylindrical. Attachment: Connate. Dimensions: 3 mm in length, 0.5 mm in width. Color: 202A.

*Pollen*.—Quantity: High. Color: 14A.

*Pistil*.—One pistil per disc floret.

*Stigma*.—Shape: Bifid, prominently exserted, standing 2 mm above corolla tube apex. Dimensions (each arm): 3 mm in length, 1 mm in width. Color: 17B.

*Style*.—Dimensions: 5 mm to 6 mm in length, 0.5 mm in diameter. Color: 151A.

*Ovary* (*observed immature*).—Position: Inferior. Shape: Cylindrical. Dimensions: 5 mm in length, 1 mm in width. Color: 150D.

*Ovary* (*observed immature only*).—Position: Inferior. Color: N144A. Shape: Globose. Dimensions: 1.5 mm in diameter.

Seed:

*Quantity*.—Sparse.

*Shape*.—Narrow fusiform with barbed pappus at apex.

*Dimensions*.—20 mm in length, 2 mm in diameter.

*Color*.—N199A.

COMPARISONS WITH PARENTS

The ray florets of 'VG001' are cherry-red or wine-red in color, whereas the flowers of the male parent are dark mahogany-red.

The flowers of the female parent are double and light pink in color, whereas the flowers of 'VG001' are single and cherry-red or wine-red in color.

In addition, plants of 'VG001' are more floriferous than plants of either of its parents.

COMPARISONS WITH COMMERCIAL VARIETIES

The closest variety of *Cosmos atrosanguineus* known to the inventor is *Cosmos* Plant known as '3013/01' (U.S. Plant Pat. No. 21,879). The flowers (inflorescences) of 'VG001' are larger (6 cm to 9 cm in diameter) than the flowers of *Cosmos* '3013/13' which are 4 cm in diameter.

In addition, the flowers of 'VG001' are cherry-red in color whereas the flowers of '3013/01' are dark maroon in color.

I claim:

1. A new and distinct cultivar of *Cosmos* plant named 'VG001' as described and illustrated herein.

* * * * *